United States Patent [19]

Skuballa et al.

[11] Patent Number: 4,618,626
[45] Date of Patent: Oct. 21, 1986

[54] NOVEL CARBACYCLIN ESTERS, PROCESS FOR THE PREPARATION THEREOF, AND THEIR USE AS MEDICINAL AGENTS

[75] Inventors: Werner Skuballa; Bernd Radüechel; Helmut Vorbrueggen, all of Berlin; Gerda Mannesmann, Cologne; Bob Nieuweboer; Michael-Harold Town, both of Berlin, all of Fed. Rep. of Germany

[73] Assignee: Schering Aktiengesellschaft, Berlin and Bergkamen, Fed. Rep. of Germany

[21] Appl. No.: 777,535

[22] Filed: Sep. 16, 1985

Related U.S. Application Data

[63] Continuation of Ser. No. 499,687, May 31, 1983, abandoned.

[30] Foreign Application Priority Data

May 28, 1982 [DE] Fed. Rep. of Germany ........ 3221193

[51] Int. Cl.⁴ .................. C07C 177/00; A61K 31/557
[52] U.S. Cl. .................................... 514/530; 560/116; 560/119
[58] Field of Search ................. 514/530; 560/116, 119

[56] References Cited

U.S. PATENT DOCUMENTS 4,238,414 12/1980 Morton .............................. 564/453

Primary Examiner—Robert Gerstl
Attorney, Agent, or Firm—Millen & White

[57] ABSTRACT

Carbacyclin esters of Formula I

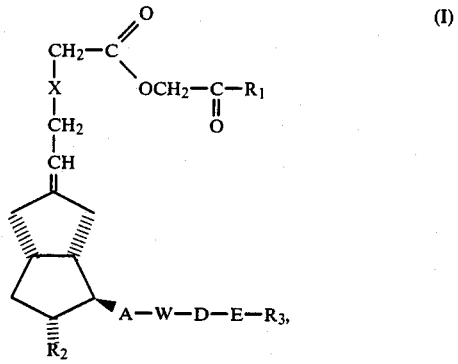

wherein
$R_1$ is an unsubstituted or substituted aromatic residue,
$R_2$ is a free or functionally modified hydroxy group,
$R_3$ is an alkyl or cycloalkyl group, or an optionally substituted aryl group, or a heterocyclic group,
X is an oxygen atom or the group $-CH_2-$,
A is a $-CH_2-CH_2-$, trans$-CH=CH-$, or $-C\equiv C-$group,
W is a free or functionally modified hydroxymethylene group or a free or functionally modified

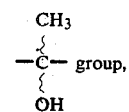

wherein the OH-group can be in the α- or β-position
D is the group

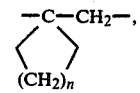

a straight-chain saturated alkylene group of 1–5 carbon atoms, a branched, saturated or a straight-chain or branched, unsaturated alkylene group of 2–5 carbon atoms, which groups can optionally be substituted by fluorine atoms,
E is a direct bond, a $-C\equiv C-$group, or a $-CR_4=CR_5-$ group wherein $R_2$ and $R_5$ mean a hydrogen atom or an alkyl group of 1–5 carbon atoms;
are useful as blood-pressure-lowering agents, inter alia.

31 Claims, No Drawings

NOVEL CARBACYCLIN ESTERS, PROCESS FOR THE PREPARATION THEREOF, AND THEIR USE AS MEDICINAL AGENTS

This is a continuation, of application Ser. No. 499,687 filed May 31, 1983 now abandoned.

BACKGROUND OF THE INVENTION

The present invention relates to novel carbacyclin esters, a process for their preparation, and their use as medicinal agents.

(5E)- and (5Z)-6a-carbaprostaglandin $I_2$ analogs are disclosed in German Unexamined Laid-Open Application DOS Nos. 2,845,770; 2,900,352; 2,902,442; 2,904,655; 2,909,088; 3,209,702; 3,204,443; 3,048,906; and 2,912,409, all of whose disclosures are incorporated by reference herein.

The nomenclature of the compounds of this invention is based on a proposal by Morton and Brokaw (J. Org. Chem. 44 : 2880 [1979]). The synthesis of these compounds yields in all cases two double-bond isomers characterized by the symbols (5E) or (5Z). The two isomers of this prototype are clarified by the following structural formule:

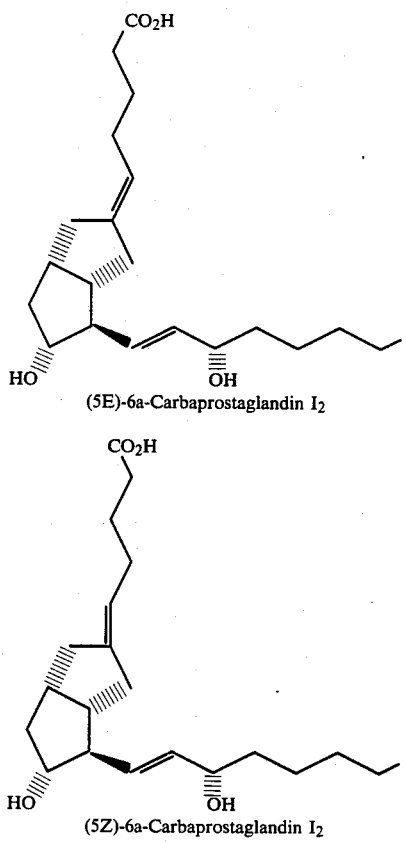

(5E)-6a-Carbaprostaglandin $I_2$ (5Z)-6a-Carbaprostaglandin $I_2$

It is known from the very voluminous state of the art of prostacyclins and their analogs that this class of compounds is suited for the treatment of mammals, including man, because of its biological and pharmacological properties. The use of these compounds as medicinal agents, however, frequently meets with difficulties since their period of effectiveness is too short for therapeutic purposes. All structural modifications in these compounds are aimed at increasing the duration of their effectiveness as well as their selectivity of efficacy.

SUMMARY OF THE INVENTION

Accordingly, it is an object of this invention to provide compounds having such improved properties.

Upon further study of the specification and appended claims, further objects and advantages of this invention will become apparent to those skilled in the art.

These objects have been achieved based on the finding that the phenacyl-type esters of carbacyclin derivatives possess a markedly longer effect than the free acids of the carbacyclin derivatives.

Such compounds have bronchodilatory effects and are suitable for inhibition of thrombocyte aggregation, for lowering blood pressure by way of vasodilation, and for inhibiting gastric acid secretion.

Thus, this invention concerns carbacyclin esters of Formula I

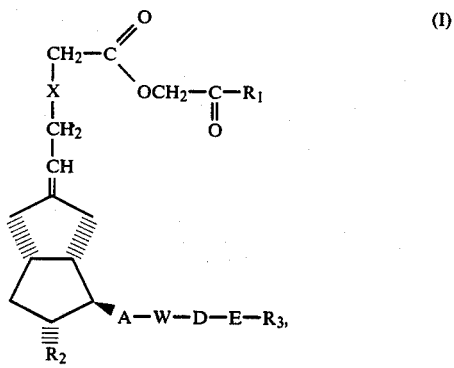

wherein $R_1$ is unsubstituted or substituted aryl, $R_2$ is free or functionally modified hydroxy, $R_3$ is alkyl or cycloalkyl or optionally substituted aryl, or a heterocyclic group, X is oxygen or —$CH_2$—, A is —$CH_2$—$CH_2$—, trans—CH=CH—, or —C≡C—, W is free or functionally modified hydroxymethylene or free or functionally modified

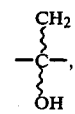

wherein the OH-group can be in the α- or β-position, D is

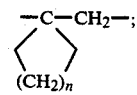

straight-chain, saturated alkylene of 1–5 carbon atoms; branched, saturated- or straight-chain or branched, unsaturated-alkylene of 2–5 carbon atoms; all of which groups can optionally be substituted by fluorine atoms, n is 0–4, E is a direct bond, —C≡C—, or —CR₄=CR₅—, wherein R₄ and R₅ are each independently hydrogen or alkyl of 1-5 carbon atoms.

DETAILED DISCUSSION

The compounds of Formula I include (5E)- as well as (5Z)-isomers.

Suitable unsubstituted aromatic residues $R_1$ include phenyl, α-naphthyl, or β-naphthyl, all of which can be substituted by 1-3 $C_1$-$C_4$-alkoxy groups, by 1-3 halogen atoms (F, Cl, or Br) or by 1-3 phenyl groups, which latter, in turn, can be substituted by 1-3 halogen atoms, such as F, Cl, or Br. Single substitutions are preferred in each case, among these the substitutions with phenyl, $C_1$-$C_2$-alkoxy, chlorine, or bromine.

The hydroxy groups $R_2$ and those in W can be functionally modified, for example by etherification or esterification, wherein the free or modified hydroxy groups in W can be in the α- or β-position, free hydroxy groups being preferred.

Ether and acyl residues include all of those known to those skilled in the art. Readily cleavable ether residues are preferred, such as, for example, the tetrahydropyranyl, tetrahydrofuranyl, α-ethoxyethyl, trimethylsilyl, dimethyl-tert-butylsilyl, and tribenzylsilyl residues. Suitable acyl residues also include those known to persons skilled in the art; examples include acetyl, propionyl, butyryl, benzoyl, e.g., acyl groups derived from a $C_{1-15}$-hydrocarbon carboxylic or sulfonic acid.

Suitable aliphatic groups $R_3$ include straight- and branched-chain, saturated and unsaturated aliphatic residues, preferably saturated ones, of 1-10, especially 1-7 carbon atoms; these can optionally be substituted by $C_{6-10}$-aryl, which latter can be substituted, if desired, e.g., as for the substituted aryl groups discussed below for $R_3$. Examples include alkyl and alkenyl groups, e.g., methyl, ethyl, propyl, butyl, isobutyl, tert-butyl, pentyl, hexyl, heptyl, octyl, butenyl, isobutenyl, propenyl, pentenyl, hexenyl, benzyl, and p-chlorobenzyl.

Suitable cycloalkyl groups $R_3$ contain 3-10, preferably 5 or 6 carbon atoms in the ring. The rings can optionally be substituted by alkyl of 1-4 carbon atoms. Examples include cyclopentyl, cyclohexyl, methylcyclohexyl, and adamantyl.

Examples of substituted or unsubstituted aryl groups $R_3$ include: phenyl, 1-naphthyl and 2-naphthyl, each of which can be substituted by 1-3 halogen atoms; a phenyl group; 1-3 alkyl groups of 1-4 carbon atoms; or a chloromethyl, fluoromethyl, trifluoromethyl, carboxy, $C_1$-$C_4$-alkoxy, or hydroxy group. Substitution in the 3- and 4-positions on the phenyl ring is preferred, for example by fluorine, chlorine, $C_1$-$C_4$-alkoxy, or trifluoromethyl, or in the 4-position by hydroxy.

Suitable heterocyclic groups $R_3$ include 5- or 6-membered heterocycles containing at least one hetero atom, preferably nitrogen, oxygen, or sulfur, the remainder being C-atoms. Examples include 2-furyl, 2-thienyl, 2-pyridyl, -3-pyridyl, 4-pyridyl, 3-furyl, 3-thienyl, and others.

Suitable aliphatic groups D include straight-chain, saturated alkylene groups of 1-5 carbon atoms or branched-chain, saturated or straight-chain or branched, unsaturated aliphatic groups of 2-5 carbon atoms, all optionally substituted by fluorine atoms, 1,2-methylene (>CH₂), or 1,1-trimethylene

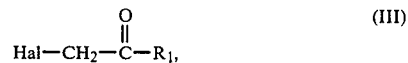

Examples include: alkylene, alkenylene, e.g., methylene, fluoromethylene, ethylene, 1,2-propylene, ethylethylene, trimethylene, tetramethylene, pentamethylene, 1-methyltetramethylene, 1-methyltrimethylene, 1,1-tri-methylenethylene, etc.

Especially preferred compounds of this invention are those with E as —C≡C— or —CR₄=CR₅— wherein R₄ and R₅ are alkyl of 1-5 carbon atoms.

The present invention furthermore relates to a process for preparing carbacyclin esters of Formula I, comprising conventionally esterifying, in the presence of a base, a compound of Formula II

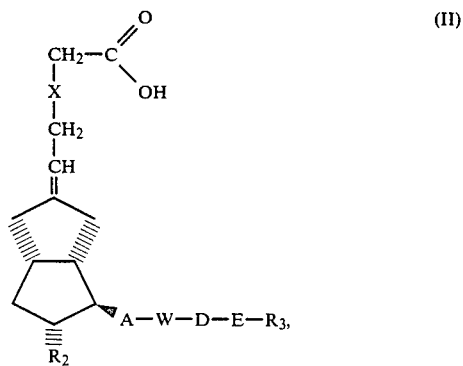

wherein $R_2$, $R_3$, X, A, W, D, and E are as defined above, optionally after conventional blockage of any free hydroxy groups present, with an ω-haloketone of Formula III $$Hal—CH_2—\overset{O}{\underset{\|}{C}}—R_1, \qquad (III)$$

wherein
$R_1$ is as defined above and
Hal represents the halogens, Cl, Br, and, optionally, subsequently liberating blocked hydroxy groups, or esterifying or etherifying free hydroxy groups, or separating the products into its isomers.

The reaction of the compound of Formula II with an ω-haloketone of Formula III is conducted at temperatures of −60° C. to 60° C., preferably 10°-40° C., in an inert solvent, e.g. acetone, acetonitrile, dimethylacetamide, dimethylformamide, or dimethyl sulfoxide. Suitable bases are those known to persons skilled in the art for such esterifications, preferably tertiary bases, for example, triethylamine, trimethylamine, tributylamine, trioctylamine, pyridine, N,N-diethylisopropylamine, and also Ag₂O, Na₂CO₃, K₂CO₃, NaHCO₃, KHCO₃, etc.

The compounds of Formula II are known from the aforementioned references, inter alia. The compounds of Formula III are known from the literature. All of these are readily preparable using fully conventional procedures.

The functional modification of the free OH-groups takes place according to methods known to those skilled in the art. In order to introduce the ether blocking groups, for example, the reaction is carried out with dihydropyran in methylene chloride or chloroform with the use of an acidic condensation agent, e.g. p-toluenesulfonic acid. The dihydropyran is used in excess, preferably in four to ten times the amount theoretically required. The reaction is normally completed at 0° to 30° C. after 15-30 minutes.

The acyl blocking groups can be introduced by conventionally reacting a compound of Formula I with a carboxylic acid derivative, e.g. an acid chloride, acid anhydride, etc.

The liberation of a functionally modified OH—group to obtain the compounds of Formula I also takes place according to methods known per se. For example, ether blocking groups are split off in an aqueous solution of an organic acid, e.g. acetic acid, propionic acid, etc., or in an aqueous solution of an inorganic acid, e.g. hydrochloric acid. To improve solubility, a watermiscible, inert organic solvent is suitably added. Organic solvents that can be used include, for example, alcohols, such as methanol and ethanol, and ethers, such as dimethoxyethane, dioxane, and tetrahydrofuran. Tetrahydrofuran is preferably employed. The splitting-off step is preferably carried out at temperatures of 20° to 80° C.

The silyl ether blocking groups are split off, for example, with tetrabutylammonium fluoride. Examples of suitable solvents include tetrahydrofuran, diethyl ether, dioxane, methylene chloride, etc. The splitting-off process is preferably conducted at temperatures of 0° to 80° C.

The acyl groups can be saponified, for example, with alkali or alkaline earth metal carbonates or hydroxides in an alcohol or in the aqueous solution of an alcohol. Aliphatic alcohols can be utilized in this connection, e.g. methanol, ethanol, butanol, etc., preferably methanol. Suitable alkali metal carbonates and hydroxides include potassium and sodium salts, but the potassium salts are preferred. Examples of suitable alkaline earth metal carbonates and hydroxides include calcium carbonate, calcium hydroxide, and barium carbonate. The reaction takes place at −10° to 70° C., preferably at 25° C.

The compounds of this invention have blood-pressure-lowering and bronchodilatory effects. They are also suitable for inhibiting thrombocyte aggregation. Consequently, the novel carbacyclin derivatives of Formula I are valuable pharmaceutically active agents. Moreover, with a similar spectrum of activity, they exhibit a higher specificity as compared with corresponding prostacyclins and, above all, an essentially longer efficacy. As compared with PGI$_2$, they are distinguished by higher stability. The high tissue specificity of the novel carbacyclin esters is demonstrated in a study on smooth-muscle organs, such as, for example, on the guinea pig ileum or on the isolated rabbit trachea, where a substantially lower stimulation is observed than in the administration of natural prostaglandins of the E-, A-, or F-type.

The novel carbacyclin analogs exhibit the properties typical for prostacyclins, such as, for example, lowering of peripheral arterial and coronary vascular resistance, inhibition of thrombocyte aggregation and dissolution of platelet thrombi, myocardial cytoprotection and thus lowering of systemic blood pressure without simultaneously lowering stroke volume and coronary blood flow; treatment for strokes, prophylaxis and therapy of coronary heart disease, coronary thrombosis, cardiac infarction, peripheral arterial diseases, arteriosclerosis and thrombosis, prophylaxis and therapy of ischemic attacks of the CNS system, therapy for shock, inhibition of bronchoconstriction, inhibition of gastric acid secretion, cytoprotection for gastric and intestinal mucosa, cytoprotection in liver and pancreas, antiallergic properties, lowering of pulmonary vascular resistance and pulmonary blood pressure, promotion of kidney blood flow, utilization in place of heparin or as an adjuvant in dialysis of hemofiltration, preservation of blood plasma stores, especially blood platelet stores, inhibition of labor, treatment of gestational toxicosis, enhancement of cerebral blood flow, etc. Besides, the novel carbacyclin derivatives exhibit antiproliferative and antidiarrheogenic properties. The carbacyclins of this invention also can be utilized in combination, for example, with β-blockers or diuretics.

The dosage of the compounds is usually 1–1,500 μg/kg/day when administered to human patients. The unit dosage in combination with a pharmaceutically acceptable carrier, is usually 0.01–100 mg.

Upon systemic administration, the novel carbacyclin esters show a markedly prolonged efficacy, for example as compared with the free acids.

The active agents of this invention thus can serve, in conjunction with the auxiliary agents known and customary in galenic pharmacy, for example for the production of blood-pressure-lowering drugs. Thus, the invention also concerns medicinal agents based on the compounds of Formula I in combination with conventional auxiliary agents and excipients.

The pharmacologically active compounds of this invention can be processed in accordance with conventional methods of galenic pharmacy to produce medicinal agents, especially for oral administration to mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

The compounds of this invention can be administered analogously to PGI$_2$ what concerns the parenteral administration The novel prostaglandin analogs of this invention are substantially more selective with regard to potency, as compared with known PG analogs in causing prostaglandin-like biological responses, and have a substantially longer duration of biological activity. Accordingly, each of these novel prostaglandin analogs is surprisingly and unexpectedly more useful than one of the corresponding conventional prostaglandins for at least one of the pharmacological purposes indicated above because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(5E)-(16RS)-16-Methyl-18,18,19,19-tetradehydro-6a-carbaprostaglandin $I_2$ 4-Phenylphenacyl Ester 108 mg of (5E)-(16RS)-16-methyl-18,18,19,19-tetradehydro-6a-carbaprostaglandin I2 is dissolved in 3 ml of acetone and combined with 87 mg of ω-bromo-4-phenylacetophenone and 1 ml of triethylamine; the mixture is agitated overnight at room temperature under argon. Then the mixture is diluted with 200 ml of ether and shaken twice with respectively 10 ml of water. After drying over $Na_2SO_4$, the organic phase is evaporated under vacuum to dryness. After purification with preparative thin-layer chromatography $CH_2Cl_2$/isopropanol (9+1) and elution with ethyl acetate, 151.4 mg of the title compound is obtained as an oil.

IR ($CHCl_3$): 3600, 2930, 1742, 1700, 1605, 970 cm$^{-1}$.

EXAMPLE 2

(5E)-(16RS)-16-Methyl-3-oxa-18,18,19,19-tetradehydro-6a-carbaprostaglandin $I_2$ Phenacyl Ester Analogously to Example 1, this compound is produced from (5E)-(16RS)-16-methyl-3-oxa-18,18,19,19-tetradehydro-6a-carbaprostaglandin and ω-bromoacetophenone.

IR ($CHCl_3$): 3600, 3400 (broad), 2925, 1740, 1705, 1600, 970 cm$^{-1}$.

EXAMPLE 3

(5E)-(16RS)-13,14-Didehydro-16-methyl-18,18,19,19-tetradehydro-6a-carbaprostaglandin $I_2$ 4-Phenylphenacyl Ester Produced analogously to Example 1 from (5E)-(16RS)13,14-didehydro-16-methyl-18,18,19,19-tetradehydro-6a-carbaprostaglandin I2 and ω-bromo-4-phenylacetophenone.

IR ($CHCl_3$): 3600, 3400, 2930, 1740, 1704, 1605 Cm$^{-1}$.

EXAMPLE 4

(5E)-18,18,19,19-Tetradehydro-16,16-trimethylene-6a-carbaprostaglandin $I_2$4-Phenylphenacyl Ester Prepared analogously to Example 1 from (5E)-18,18,19,19-tetradehydro-16,16-trimethylene-6a-carbaprostaglandin I2 and ω-bromo-4-phenylacetophenone.

IR ($CHCl_3$): 3600, 3400 (broad), 2925, 1738, 1700, 1605, 970 cm$^{-1}$.

EXAMPLE 5

(5E)-(16RS)-16-Methyl-18,18,19,19-tetradehydro-6a-carbaprostaglandin $I_2$2,5-Dimethoxyphenacyl Ester Analogously to Example 1, this compound is produced from (5E)-(16RS)-16-methyl-18,18,19,19-tetradehydro-6a-carbaprostaglandin I2 and ω-bromo-2,5-dimethoxyacetophenone.

IR ($CHCl_3$): 3600, 3400 (broad), 2930, 1745, 1700, 1603, 970 cm$^{-1}$.

EXAMPLE 6

(5E)-(16RS)-16-Methyl-18,18,19,19-tetradehydro-6a-carbaprostaglandin $I_2$ Phenacyl ester Prepared analogously to Example 1 from (5E)-(16RS)-16-methyl-18,18,19,19-tetradehydro-6a-carbaprostaglandin I2 and ω-bromoacetophenone.

IR ($CHCl_3$): 3600, 2925, 1743, 1705, 1600, 970 cm$^{-1}$.

EXAMPLE 7

(5F)-(16RS)-13,14-Didehydro-16-methyl-18,18,19,19-tetradehydro-6a-carbaprostaglandin $I_2$ Phenacyl Ester Produced analogously to Example 1 from (5E)-(16RS)-13,14-didehydro-16-methyl-18,18,19,19-tetradehydro-6a-carbaprostaglandin I2 and ω-bromoacetophenone.

IR ($CHCl_3$): 3600, 3400 (broad), 2930, 1740, 1700, 1605 cm$^{-1}$.

EXAMPLE 8

(5E)-18,18,19,19-Tetradehydro-16,16-trimethylene-6a-carbaprostaglandin $I_2$ Phenacyl Ester Prepared analogously to Example 1 from (5E)-18,18,19,19-tetradehydro-16,16-trimethylene-6a-carbaprostaglandin I2 and ω-bromoacetophenone.

IR ($CHCl_3$): 3600, 3400, 2950, 1745, 1702, 1600, 965 cm$^{-1}$.

EXAMPLE 9

(5E)-16,16-Dimethyl-18,18,19,19-tetradehydro-6a-carbaprostaglandin $I_2$ Phenacyl Ester Produced analogously to Example 1 from (5E)-16,16-dimethyl-18,18,19,19-tetradehydro-6a-carbaprostaglandin I2 and ω-bromoacetophenone.

IR ($CHCl_3$): 3600, 3400, 2925, 1743, 1705, 1600, 970 cm$^{-1}$.

EXAMPLE 10

(5E)-(16RS)-16,20-Dimethyl-18,18,19,19-tetradehydro-6a-carbaprostaglandin $I_2$ Phenacyl Ester Prepared analogously to Example 1 from (5E)-(16RS)-16,20-dimethyl-18,18,19,19-tetradehydro-6a-carbaprostaglandin I2 and ω-bromoacetophenone.

IR (CHCl₃): 3600, 3400 (broad), 2930, 1745, 1701, 1605, 965 cm⁻¹.

EXAMPLE 11

(5E)-20-Methyl-18,18,19,19-tetradehydro-16,16-trimethylene-6a-carbaprostaglandin I₂ Phenacyl Ester Produced analogously to Example 1 from (5E)-20-methyl-18,18,19,19-tetradehydro-16,16-trimethylene-6a-carbaprostaglandin I₂ and ω-bromoacetophenone.

IR (CHCl₃): 3600, 3400 (broad), 2925, 1740, 1700, 1600, 970 cm¹.

EXAMPLE 12

(5E)-13,14-Didehydro-20-methyl-18,18,19,19-tetradehydro-16,16-trimethylene-6a-carbaprostaglandin I₂ Phenacyl Ester Prepared analogously to Example 1 from (5E)-13,14-didehydro-20-methyl-18,18,19,19-tetradehydro-16,16-trimethylene-6a-carbaprostaglandin I₂ and ω-bromoacetophenone.

IR (CHCl₃): 3600, 3400 (broad), 2930, 1745, 1700, 1605 cm⁻¹.

EXAMPLE 13

(5E)-(16RS)-16,19-Dimethyl-18,19-didehydro-6-acarbaprostaglandin I₂ Phenacyl Ester Produced analogously to Example 1 from (5E)-(16RS)-16,19-dimethyl-18,19-didehydro-6a-carbaprostaglandin I₂ and ω-bromoacetophenone.

IR (CHCl₃): 3600, 3400, 2930, 1745, 1705, 970 cm⁻¹.

EXAMPLE 14

(5E)-(16RS)-16-Methyl-18,18,19,19-tetradehydro-6a-carbaprostaglandin I₂ 4-Methoxyphenacyl Ester Prepared analogously to Example 1 from (5E)-(16RS)-16-methyl-18,18,19,19-tetradehydro-6a-carbaprostaglandin I₂ and ω-bromo-4-methoxyacetophenone.

IR (CHCl₃): 3600, 3400, 2925, 1740, 1700, 1600, 970 cm⁻¹.

EXAMPLE 15

(5E)-(16RS)-16-Methyl-18,18,19,19-tetradehydro-6a-carbaprostaglandin I₂4-Chlorophenacyl Ester Analogously to Example 1, this compound is produced from (5E)-(16RS)-16-methyl-18,18,19,19-tetradehydro-6a-carbaprostaglandin I₂ and ωbromo-4-chloroacetophenone.

IR: 3600, 3400 (broad), 2935, 1743, 1703, 970 cm⁻¹.

EXAMPLE 16

(5E)-(16RS)-16-Methyl-18,18,19,19-tetradehydro-6a-carbaprostaglandin I₂ 4-Bromophenacyl Ester Produced analogously to Example 1 from (5E)(16RS)-16-methyl-18,18,19,19-tetradehydro-6a-carbaprostaglandin I₂ and ω,4-dibromoacetophenone.

IR: 3610, 3400 (broad), 2930, 1744, 1702, 972 cm⁻¹.

EXAMPLE 17

(5E)-(16RS)-16-Methyl-18,18,19,19-tetradehydro-6a-carbaprostaglandin I2 2-Methoxyphenacyl Ester Prepared analogously to Example 1 from (5E)-(16RS)-16-methyl-18,18,19,19-tetradehydro-6a-carbaprostaglandin I₂ and ω-bromo-2-methoxyacetophenone.

IR: 3600, 3400 (broad), 2930, 1744, 1700, 970 cm⁻¹.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A carbacyclin of the formula

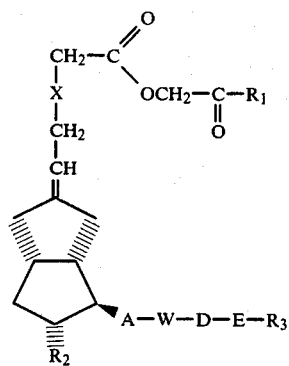

wherein $R_1$ is phenyl, α-naphthyl or β-naphthyl; or phenyl, α-naphthyl or β-naphthyl each substituted by 1-3 $C_{1-4}$-alkoxy groups, 1-3 halo atoms, 1-3 phenyl groups or 1-3 phenyl groups substituted by 1-3 halo atoms;

$R_2$ is OH or OR:

$R_3$ is (a) $C_{2-10}$-alkenyl, (b) $C_{1-10}$ alkyl, (c) $C_{2-10}$-alkenyl or $C_{1-10}$ alkyl each substituted by $C_{6-10}$ aryl or $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group, (d) $C_{3-10}$ cycloalkyl, (e) $C_{3-10}$ cycloalkyl substituted by $C_{1-4}$ alkyl, (f) $C_{6-10}$ aryl, (g) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group, or (h) an aromatic heterocycle of 5 or 6 ring atoms one of which is O, N or S, the remainder being carbon atoms;

X is an oxygen atom or —CH₂—;

A is —CH₂—CH₂—, trans—CH=CH—, or —C≡C—;

W is —CHOR— or

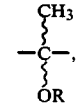

wherein the OR-group can be in the -or -position,

D is

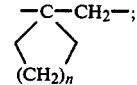

—CH₂—CH₂—; —CH₂—CH₂ 1-substituted by CH₃ or di—CH₃ or substituted by 1,2-methylene; or one of the former substituted by fluorine;

n is 0-4;

E is —C≡C, or —CR₄=CR₅—wherein R₄ and R₅ each independently is hydrogen or alkyl or 1-5 carbon atoms, and R is H, tetrahydropyranyl, tetrahydrofuranyl, α-ethoxyethyl, trimethylsilyl, dimethyl-tert-butysilyl, tribenzylsilyl or an acyl group of a $C_{1-15}$-hydrocarbon carboxylic or sulfonic acid.

2. A compound of claim 1 wherein R₁ is phenyl or phenyl substituted by one of $C_1$-$C_2$-alkoxy, phenyl, Cl or Br.

3. A compound of claim 1 wherein R is H.

4. A compound of claim 1 wherein the first carbon atom of D is substituted by CH₃, di-CH₃ or

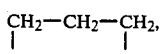

5. A compound of claim 1 wherein A is trans-CH=CH— or —C≡C.

6. A compound of claim 1 wherein E is —C≡C—.

7. A compound of claim 1 wherein E is —CR₄=CR₅— wherein both R₄ and R₅ are $C_{1-5}$-alkyl.

8. A compound of claim 1 wherein R₃ is alkyl.

9. A compound of claim 1 wherein AWDER₃ is

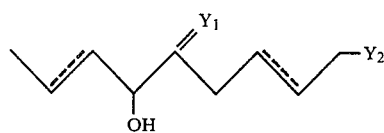

wherein represents a double or triple bond; =Y₁, is CH₃, H;

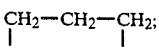

or CH₃,CH₃; and Y₂ is H or CH₃.

10. (5E)-(16RS)-16-Methyl-18,18,19,19-tetradehydro-6a-carbaprostaglandin I₂4-phenylphenacyl ester, a compound of claim 1.

11. (5E)-(16RS)-16-Methyl-3-oxa-18,18,19,19-tetradehyro-6a-carbaprostaglandin I₂ phenacyl ester, a compound of claim 1.

12. (5E)-(16RS)-13,14-Didehydro-16-methyl-18,18,19,19- tetradehydro-6a-carbaprostaglandin I₂4-phenylphenacyl ester, a compound of claim 1.

13. (5E)-18,18,19,19-Tetradehydro-16,16-trimethylene-6a-carbaprostaglandin I₂4-phenylphenacyl ester, a compound of claim 1.

14. (5E)-(16RS)-16-Methyl-18,18,19,19-tetradehydro-6a-carbaprostaglandin I₂ 2,5-dimethoxyphenacyl ester, a compound of claim 1.

15. (5E)-(16RS)-16-Methyl-18,18,19,19-tetradehydro-6a-carbaprostaglandin I₂ phenacyl ester, a compound of claim 1.

16. (5E)-(16RS)-13,14-Didehydro-16-methyl-18,18,19,19-tetradehydro-6a-carbaprostaglandin I₂ phenacyl ester, a compound of claim 1.

17. (5E)-18,18,19,19-Tetradehydro-16,16-trimethylene-6a-carbaprostaglandin I₂ phenacyl ester, a compound of claim 1.

18. (5E)-16,16-Dimethyl-18,18,19,19-tetradehydro-6a-carbaprostaglandin I₂ phenacyl ester, a compound of claim 1.

19. (5E)-(16RS)-16,20-Dimethyl-18,18,19,19-tetradehydro-6a-carbaprostaglandin I₂ phenacyl ester, a compound of claim 1.

20. (5E)-20-Methyl-18,18,19,19-tetradehydro-16,16-trimethylene-6a-carbaprostaglandin I₂ phenacyl ester, a compound of claim 1.

21. (5E)-13,14-Didehydro-20-methyl-18,18,19,19-tetradehydro-16,16-trimethylene-6a-carbaprostaglandin I₂ phenacyl ester, a compound of claim 1.

22. (5E)-(16RS)-16,19-Dimethyl-18,19-didehydro-6a-carbaprostaglandin I₂ phenacyl ester, a compound of claim 1.

23. (5E)-(16RS)-16-Methyl-18,18,19,19-tetradehydro-6a-carbaprostaglandin I₂ 4-methoxyphenacyl ester, a compound of claim 1.

24. (5E)-(16RS)-16-Methyl-18,18,19,19-tetradehydro-6a-carbaprostaglandin I₂ 4-chlorophenacyl ester, a compound of claim 1.

25. (5E)-(16RS)-16-Methyl-18,18,19,19-tetradehydro-6a-carbaprostaglandin I₂ 4-bromophenacyl ester, a compound of claim 1.

26. (5E)-(16RS)-16-Methyl-18,18,19,19-tetradehydro-6a-carbaprostaglandin I₂ 2-methoxyphenacyl ester, a compound of claim 1.

27. A compound of claim 1, wherein X is 0.

28. A compound of claim 1, wherein $R^1$ is phenyl substituted by 1-3-$C_{1-4}$-alkoxy groups.

29. A compound of claim 1, wherein X is —CH₂—.

30. A pharmaceutical composition comprising an amount of a compound of claim 1 effective to lower blood pressure and a pharmaceutically acceptable carrier.

31. A method of lowering blood pressure in a patient in need of such treatment comprising administering to the patient an effective amount of a compound of claim 1.

* * * * *